US009877667B2

(12) United States Patent
Doheny

(10) Patent No.: US 9,877,667 B2
(45) Date of Patent: Jan. 30, 2018

(54) METHOD FOR QUANTIFYING THE RISK OF FALLING OF AN ELDERLY ADULT USING AN INSTRUMENTED VERSION OF THE FTSS TEST

(75) Inventor: Emer P. Doheny, Dublin (IE)

(73) Assignee: CARE INNOVATIONS, LLC, Roseville, CA (US)

( * ) Notice: Subject to any disclaimer, the term of this patent is extended or adjusted under 35 U.S.C. 154(b) by 686 days.

(21) Appl. No.: 13/611,012

(22) Filed: Sep. 12, 2012

(65) Prior Publication Data

US 2014/0074442 A1    Mar. 13, 2014

(51) Int. Cl.
*A61B 5/11* (2006.01)
*G06F 19/00* (2011.01)
*A61B 5/00* (2006.01)
*G08B 21/04* (2006.01)

(52) U.S. Cl.
CPC ........... *A61B 5/1116* (2013.01); *A61B 5/1117* (2013.01); *A61B 5/7264* (2013.01); *G06F 19/3431* (2013.01); *A61B 5/7275* (2013.01); *A61B 2562/0219* (2013.01); *G08B 21/0446* (2013.01); *G08B 21/0453* (2013.01)

(58) Field of Classification Search
CPC ............ A61B 5/067; A61B 2019/5248; A61B 2562/0219; A61B 2017/00712
USPC .......................................................... 703/2
See application file for complete search history.

(56) References Cited

U.S. PATENT DOCUMENTS 3,791,375 A    2/1974 Pfeiffer
4,738,269 A    4/1988 Nashner
5,052,406 A    10/1991 Nashner
(Continued)

FOREIGN PATENT DOCUMENTS

WO    2011002788    1/2011
WO    2011016782    2/2011
WO    2012094486    7/2012

OTHER PUBLICATIONS

Emer P. Doheny, Chie Wei Fan, Timothy Foran, Barry R. Greene, Clodagh Cunningham and Rose Anne Kenny; "An Instrumented sit-to-stand test used to examine differences between older fallers and non-fallers"; Aug. 30-Sep. 3, 2011; IEEE EMBS; 33rd Annual Conference, pp. 3063-3066.*

(Continued)

*Primary Examiner* — John Breene
*Assistant Examiner* — Christine Liao
(74) *Attorney, Agent, or Firm* — Pillsbury Winthrop Shaw Pittman, LLP

(57) ABSTRACT

Methods and systems may provide for estimating falls risk based on inertial sensor data collected during a Five Times Sit-to-Stand (FTSS) test. In an embodiment, a classifier model may be trained with inertial sensor data collected from a sample of people performing the FTSS test and their self-reported falls history. In an embodiment, one or more features related to steadiness or smoothness of the person's movement may be calculated. In an embodiment, one or more features related to timing of the FTSS test, such as a total time taken to complete the FTSS test or to complete individual sit-stand-sit (SSS) phases of the test, may be calculated. In an embodiment, supervised pattern recognition techniques may train the classifier model to classify a person as being likely to fall or not being likely to fall based on FTSS-related feature values collected from that person.

13 Claims, 5 Drawing Sheets

(56) References Cited

U.S. PATENT DOCUMENTS

| | | |
|---|---|---|
| 5,209,240 A | 5/1993 | Jain |
| RE34,663 E | 7/1994 | Seale |
| 5,388,591 A | 2/1995 | De Luca et al. |
| 5,919,149 A | 7/1999 | Allum |
| 6,059,576 A | 5/2000 | Brann |
| 6,063,046 A | 5/2000 | Allum |
| 6,820,025 B2 | 11/2004 | Bachmann et al. |
| 6,852,086 B2 | 2/2005 | Atlas et al. |
| 7,141,026 B2 | 11/2006 | Arminian et al. |
| 7,361,150 B2 | 4/2008 | Berthonnaud |
| 7,526,071 B2 | 4/2009 | Drapeau |
| 7,998,092 B2 | 8/2011 | Ayni et al. |
| 8,011,229 B2 | 9/2011 | Lieberman et al. |
| 8,092,355 B2 | 1/2012 | Mortimer |
| 8,109,590 B2 | 2/2012 | Kamiar |
| 8,152,744 B2 | 4/2012 | Mukumoto |
| 8,206,325 B1 * | 6/2012 | Najafi ................. A61B 5/1116 600/587 |
| 8,261,611 B2 | 9/2012 | Kim et al. |
| 8,280,681 B2 | 10/2012 | Vock et al. |
| 8,308,665 B2 | 11/2012 | Harry et al. |
| 8,405,510 B2 | 3/2013 | Shieh |
| 8,529,448 B2 | 9/2013 | McNair |
| 8,823,526 B2 | 9/2014 | Kaiser et al. |
| 8,852,128 B2 | 10/2014 | Bhattacharya |
| 8,961,439 B2 | 2/2015 | Yang et al. |
| 8,990,041 B2 * | 3/2015 | Grabiner et al. ............. 702/141 |
| 2001/0053883 A1 | 12/2001 | Yoshimura et al. |
| 2002/0077567 A1 | 6/2002 | McLeod |
| 2004/0143452 A1 | 7/2004 | Pattillo et al. |
| 2005/0010139 A1 | 1/2005 | Aminian et al. |
| 2005/0182341 A1 | 8/2005 | Katayama et al. |
| 2005/0234309 A1 | 10/2005 | Klapper |
| 2006/0166737 A1 | 7/2006 | Bentley |
| 2006/0282017 A1 | 12/2006 | Avni et al. |
| 2007/0057786 A1 | 3/2007 | McClure et al. |
| 2007/0118043 A1 | 5/2007 | Oliver et al. |
| 2008/0146968 A1 | 6/2008 | Hanawaka et al. |
| 2008/0167580 A1 | 7/2008 | Avni et al. |
| 2008/0243265 A1 | 10/2008 | Lanier et al. |
| 2008/0281550 A1 | 11/2008 | Hogle et al. |
| 2008/0306410 A1 | 12/2008 | Kalpaxis et al. |
| 2009/0076419 A1 | 3/2009 | Namineni et al. |
| 2009/0076765 A1 | 3/2009 | Kulach et al. |
| 2009/0185772 A1 | 7/2009 | Xia et al. |
| 2009/0196206 A1 | 8/2009 | Weaver et al. |
| 2009/0216156 A1 | 8/2009 | Lengsfeld et al. |
| 2009/0240170 A1 | 9/2009 | Rowley |
| 2009/0247909 A1 | 10/2009 | Mukumoto |
| 2009/0247910 A1 | 10/2009 | Klapper |
| 2009/0260426 A1 | 10/2009 | Lieberman et al. |
| 2009/0318779 A1 | 12/2009 | Tran |
| 2010/0152622 A1 | 6/2010 | Teulings |
| 2011/0022349 A1 | 1/2011 | Stirling |
| 2011/0092860 A1 | 4/2011 | Salarian et al. |
| 2011/0118620 A1 * | 5/2011 | Scheib ......................... 600/544 |
| 2011/0119267 A1 | 5/2011 | Forman et al. |
| 2011/0162433 A1 | 7/2011 | Peng et al. |
| 2011/0184225 A1 | 7/2011 | Whitall et al. |
| 2011/0190593 A1 | 8/2011 | McNair |
| 2011/0190667 A1 | 8/2011 | Alwan |
| 2011/0213278 A1 | 9/2011 | Horak |
| 2011/0264010 A1 | 10/2011 | Williams |
| 2011/0275956 A1 | 11/2011 | Son et al. |
| 2011/0288811 A1 | 11/2011 | Greene |
| 2012/0021873 A1 | 1/2012 | Brunner |
| 2012/0059282 A1 | 3/2012 | Agichtein et al. |
| 2012/0065915 A1 | 3/2012 | Hara et al. |
| 2012/0072168 A1 | 3/2012 | Yin et al. |
| 2012/0092169 A1 | 4/2012 | Kaiser et al. |
| 2012/0101411 A1 | 4/2012 | Hausdorff et al. |
| 2012/0119904 A1 | 5/2012 | Coleman Boone et al. |
| 2012/0130266 A1 | 5/2012 | Mathan |
| 2012/0198949 A1 | 8/2012 | Xia et al. |
| 2012/0232430 A1 | 9/2012 | Boissy |
| 2012/0253234 A1 | 10/2012 | Yang et al. |
| 2012/0289791 A1 | 11/2012 | Jain et al. |
| 2012/0316843 A1 | 12/2012 | Beno et al. |
| 2013/0060512 A1 | 3/2013 | Greene |
| 2013/0123665 A1 | 5/2013 | Mariani et al. |
| 2013/0123666 A1 | 5/2013 | Giuffrida et al. |
| 2013/0123669 A1 | 5/2013 | Kinoshita et al. |
| 2013/0218053 A1 | 8/2013 | Kaiser et al. |
| 2013/0303860 A1 * | 11/2013 | Bender et al. ................. 600/300 |

OTHER PUBLICATIONS

P.A. Stalenhoef, J.P.M. Diederiks, J.A. Knottnerus, A.D.M. Kester, H.F.J.M. Crebolder, "A risk model for the prediction of recurrent falls in community-dwelling elderly: A prospective cohort study", Aug. 2002, Elsevier, Journal of Clinical Epidemiology 55 (2002), pp. 1088-1094.*

Greene, Barry R. et al., Assessment of Cognitive Decline Through Quantitative Analysis of the Timed Up and Go Test, IEEE Transactions on Biomedical Engineering, vol. 59, No. 4, Apr. 2012, pp. 988-995.

Greene, Barry R. et al., Body-worn sensor based surrogates of minimum ground clearance in elderly fallers and controls, 33rd Annual International Conference of the IEEE EMBS, Boston, Massachusetts USA, Aug. 30-Sep. 3, 2011.

Greene, Barry R. et al., Quantitative Falls Risk Assessment Using the Timed Up and Go Test, IEEE Transactions on Biomedical Engineering, vol. 57, No, 12, Dec. 2010, pp. 2918-2926.

Greene, Barry R. et al., Adaptive estimation of temporal gait parameters using body-worn gyroscopes, 32nd Annual International Conference of the IEEE EMBS, Buenos Aires, Argentina, Aug. 31-Sep. 4, 2010.

Greene, Barry R. et al., Falls risk assessment through quantitative analysis of TUG, Mar. 21, 2010.

Donovan, Karol J. et al., Shimmer: A new tool for temporal Gait analysis, 31st Annual International Conference of the IEEE EMBS, Minneapolis, Minnesota, USA, Sep. 2-6, 2009.

Doheny, Emer P., et al., A single gyroscope method for spatial gait analysis, 32nd Annual International Conference of the IEEE EMBS, Buenos Aires, Argentina, Aug. 31-Sep. 4, 2010.

McGrath, Denise et al., Estimation of minimum ground clearance (MGC) using body-work inertial sensors, Journal of Biomechanics 44 (2011), pp. 1083-1088.

Greene, Barry R. et al., An adaptive gyroscope-based algorithm for temporal gait analysis, Med Biol Eng Computn Nov. 2010, vol. 48, pp. 1251-1260.

Brach, Jennifer S., et al., "Gait Variability and the Risk of Incident Mobility Disability in Community Dwelling Older Adults," 2007, Journal of Gerontology: Medical Sciences, vol. 62A, No. 9, pp. 983-988.

Deshpande et al., "Gait speed under varied challenges and cognitive decline in older persons: a prospective study," Jul. 25, 2009, Oxford University Press on behalf of the British Geriatrics Society, pp. 509-514.

Extended European Search Report dated Dec. 12, 2014 in European Application 13177482,0.

Ferraris et al., "Procedure for Effortless In-Field Calibration of Three-Axis Rate Gyros and Acelerometers," Sensors and Materials, vol. 7, No. 5, 1995, pp. 311-330.

Foroughi, H. et al., "Robust Fall Detection Using Human Shape and Multi-class Support Vector Machine", Sixth Indian Conference on Computer Vision, Graphics & Image Processing, pp. 413-420, ISBN: 978-0-7695-3476-3, XP 031409478, Dec. 16, 2008.

Fried et al., "Frailty in Older Adults: Evidence for a Phenotype," Journal of Gernatology: Medical Sciences, 2001, vol. 56A, No, 3, pp. M146-M156.

Friedman, Jerome H., "Regularized Discriminant Analysis," Jul. 1988, Journal of the American Statistical Association, pp. 1-32.

Giansanti, "Assessment of fall-risk by means of a neural network based on parameters assessed by a wearable device during posturography", Medical Engineering & Physics, vol. 30, 2008, pp. 367-372.

(56) References Cited

OTHER PUBLICATIONS

Giansanti, "Investigation of fall-risk using a wearable device with accelerometers and rate gyroscopes", Physiol. Meas, vol. 27, Sep. 11, 2006, pp. 1081-1090.
Gkalelis et al., "Human Movement Recognition Using Fuzzy Clustering and Discrmininant Analysis," Aug. 2008, EUSIPCO.
Greene et al., Classifier Models and Architectures for EEG-Based Neonatal Seizure Detection, Physiol. Meas., 2008, pp. 1157-1178, 29, IOP Publishing, UK.
Greene et al., "Evaluation of Falls Risk in Community-Dwelling Older Adults Using Body-Worn Sensors," Regenerative and Technological Section/Original Paper, Gerontology 2012, vol. 59, pp. 472-480, along with supplementary table.
Greene et al., "Quantatative falls risk estimation through multi-sensor assessment of standing balance," Physiological Measurement, Physiol. Meas. 33 (2012), pp. 2049-2063.
Higashi, Yuji et al., "Quantitative Evaluation of Movement Using the Timed-Up-and-Go Test", IEEE Engineering in Medicine and Biology Magazine, Jul./Aug. 2008, pp. 38-46.
International Search Report and Written Opinion dated Oct. 12, 2011, for PCT/US2011/036955.
Lai, "A Hybrid Support Vector Machine and Autoregressive model for detecting gait disorders in the elderly," IEEE, 2007.
Latt, Mark D., et al., "Clininical and Physiological Assessments for Elucidating Falls Risk in Parkinson's Disease," No. 9, 2009, Movement Disorder Society, vol. 24, pp. 1280-1289.
Macon State College, Quadratic Regression, 2007.
Makary, M. A., et al., "Frailty as a Predictor of Surgical Outcomes in Older Patients," pp. 901-908, 2010.
Najafi et al., "Measurement of Stand-Sit and Sit-Stand Transitions Using a Miniature Gyroscope and Its Application in Fall Risk Evaluation in the Elderly," Aug. 2002, IEEE Transactions on Biomedical Engineering, vol. 49, No. 8.
Narayanan et al., "Longitudinal Falls Risk Estimation using Triaxial Accelerometry", IEEE Trans., vol. X, No. Y, Jul. 2009, pp. 1-8.
Pavel, Misha, "Continuous Assessment of Gait Velocity in Parkinson's Disease from Unobtrusive Measurements", 2007, 4 pages.
Pavel, Misha, "Unobtrusive Assessment of Mobility", 2006, 5 pages.
Sabatini, A. et al., "Assessment of Walking Features From Foot Inertial Sensing," IEEE Transactions on Biomedical Engineering [online], Mar. 2005 [retrieved on May 17, 2015]. Retrieved from the Internet: <http://ieeexplore.ieee.org/xpls/abs_all.jsp?arnumber=1396389>.
Salarian et al., "iTUG, a Sensitive and Reliable Measure of Mobility", IEEE Transactions on Neural Systems and Rehabilitation Engineering 2010, pp. 1-8.
Vellas et al., "One-Leg Balance is an Important Predictor of Injurious Falls in Older Persons," 1997, American Geriatrics Society, pp. 735-738.
Walsh et al., "Development and Validation of a Clinic Based Balance Assessment Technology," 33rd Annual International Conference of the IEEE EMBS, Aug. 30-Sep. 3, 2011, pp. 1327-1330.
Weiss et al., "Can an accelerometer enhance the utility of the Timed Up & Go Test when evaluating patients with Parkinson's disease?", Medical Engineering & Physics vol. 32, 2010, pp. 119-125.
Zampieri et al., The instrumented timed up and go test: potential outcome measure for disease modifying therapies in Parkinson's disease, Journal Neurology Neurosurgery and Psychiatry, Feb. 1, 2010, pp. 171-176, vol. 81, No. 2.
Extended European Search Report dated Jun. 8, 2016, in EP Application 13177483.8.
Patel S. et al., "Monitoring Motor Flucuations in Patients with Parkinson's Disease Using Wearable Sensors," IEEE Transactions on Information Technology in Biomedicine, IEEE Service Center, Los Alamitos, CA, US, vol. 13, No. 6, Nov. 2009, pp. 864-873.

\* cited by examiner

US 9,877,667 B2

METHOD FOR QUANTIFYING THE RISK OF FALLING OF AN ELDERLY ADULT USING AN INSTRUMENTED VERSION OF THE FTSS TEST

BACKGROUND

Technical Field

Embodiments generally relate to quantifying a person's risk of falling.

Discussion

Falls are a very common problem in the older population. About 30% of community dwelling elderly people 65 years or older fall each year. About 12% fall at least twice. Such falls may lead to injury, disability, or even death. Estimating a person's risk of falling may allow early clinical intervention to treat those having a high risk of falling.

SUMMARY

An embodiment of this invention relates to analyzing movement-related data that are collected from a person performing the Five Times Sit-to-Stand (FTSS) test. The FTSS test assesses a person's mobility and balance. During the FTSS, a person must fully stand up and sit back down five times as quickly as possible. The total time taken to perform the FTSS test may provide some indication of falls risk. This embodiment is an instrumented FTSS (iFTSS) technique that further or alternatively relies on the movement-related data collected from the FTSS test. For this iFTSS technique, one or more (e.g., two) inertial sensors, such as accelerometers, may be attached to the person performing the test. Acceleration data associated with the FTSS test may be received from the accelerometers. Other data, such as a total time taken to complete the FTSS test, or the person's age, may also be received.

In an embodiment, the acceleration data or other FTSS-related data may be used as part of a supervised pattern recognition technique that generates an iFTSS model (e.g., a function) for classifying a person as being likely or not likely to fall based on his or her FTSS-derived data. For example, the model may be generated from a sample group of people who perform the FTSS test. Acceleration data collected from each person in the sample may be associated with that person's self-reported falls history (e.g., of the last five years), which may include whether that person has fallen or how many times that person has fallen. A fall may be defined as an unexpected loss of balance resulting in coming to rest on the floor, the ground, or an object below the knee level. A classifier model, such as a linear discriminant model, may be trained with the acceleration data collected from each person in the sample and the person's corresponding falls history. In an embodiment, the trained classifier model may then be used to classify a person outside the sample as being likely to fall or not likely to fall based on FTSS-derived data collected from that person. The trained classifier model may allow a person to estimate his or her risk of falling in a non-clinical setting.

These and other embodiments are described in more detail below.

BRIEF DESCRIPTION OF THE DRAWINGS

The various features of the embodiments will become apparent to one skilled in the art by reading the following specification and appended claims, and by referencing the following drawings, in which:

DETAILED DESCRIPTION

Embodiments may provide for a system and method for generating classifier models (e.g., classifier functions) or other models that estimate a person's falls risk based on FTSS-derived data collected from that person. The FTSS-derived data may include inertial sensor data, and may also include clinical parameters such as total time taken to complete the FTSS test or such as age of the person performing the FTSS test.

In an embodiment, a person performing the FTSS test may be asked to refrain from vigorous exercise on the previous day and on the day of the test. In an embodiment, the person may be asked to eat a light breakfast, light lunch, and a light snack, and to refrain from drinking caffeinated drinks. In an embodiment, one or more times at which the person took medication may be recorded. During the test, the person may be asked to keep his or her arms folded and to fully stand up and sit back down five times as quickly as possible.

Figure 1:
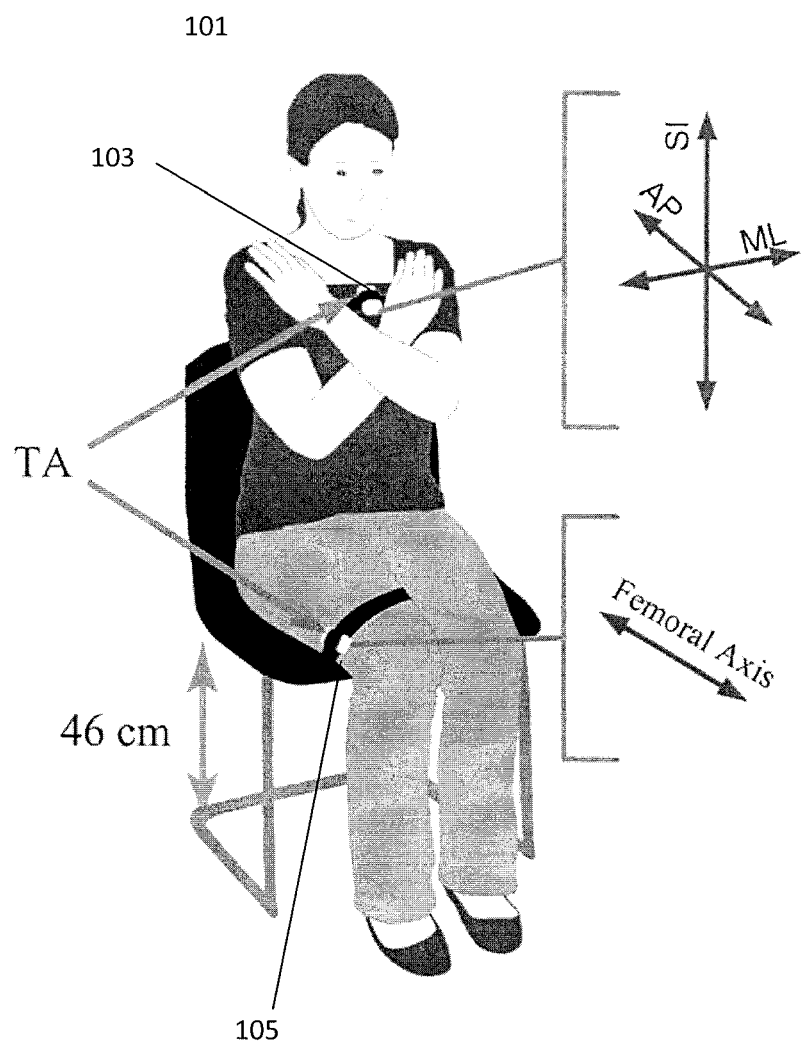
FIG. 1 illustrates an example setup for an individual to perform the Five Times Sit-to-Stand (FTSS) test and for collecting inertial sensor data from the individual.

In an embodiment, inertial sensor data associated with the FTSS test may be received from one or more inertial sensors attached to the person performing the test. For example, as illustrated in FIG. 1, a first tri-axial accelerometer 105 may be attached at the person's anterior thigh, and a second tri-axial accelerometer 103 may be attached at the person's sternum. The first tri-axial accelerometer 105 may be positioned such that one of its axes aligns with a longitudinal line of the person's femur (i.e., with the person's femoral axis). The second tri-axial accelerometer 103 may be positioned such that its axes measure the person's acceleration along his or her superior-inferior (SI) axis, anterior-posterior (AP) axis, and medial-lateral (ML) axis.

In an embodiment, each accelerometer 103, 105 may be programmed to sample each axis at a rate of 102.4 Hz using custom developed TinyOS firmware.

Figure 2:
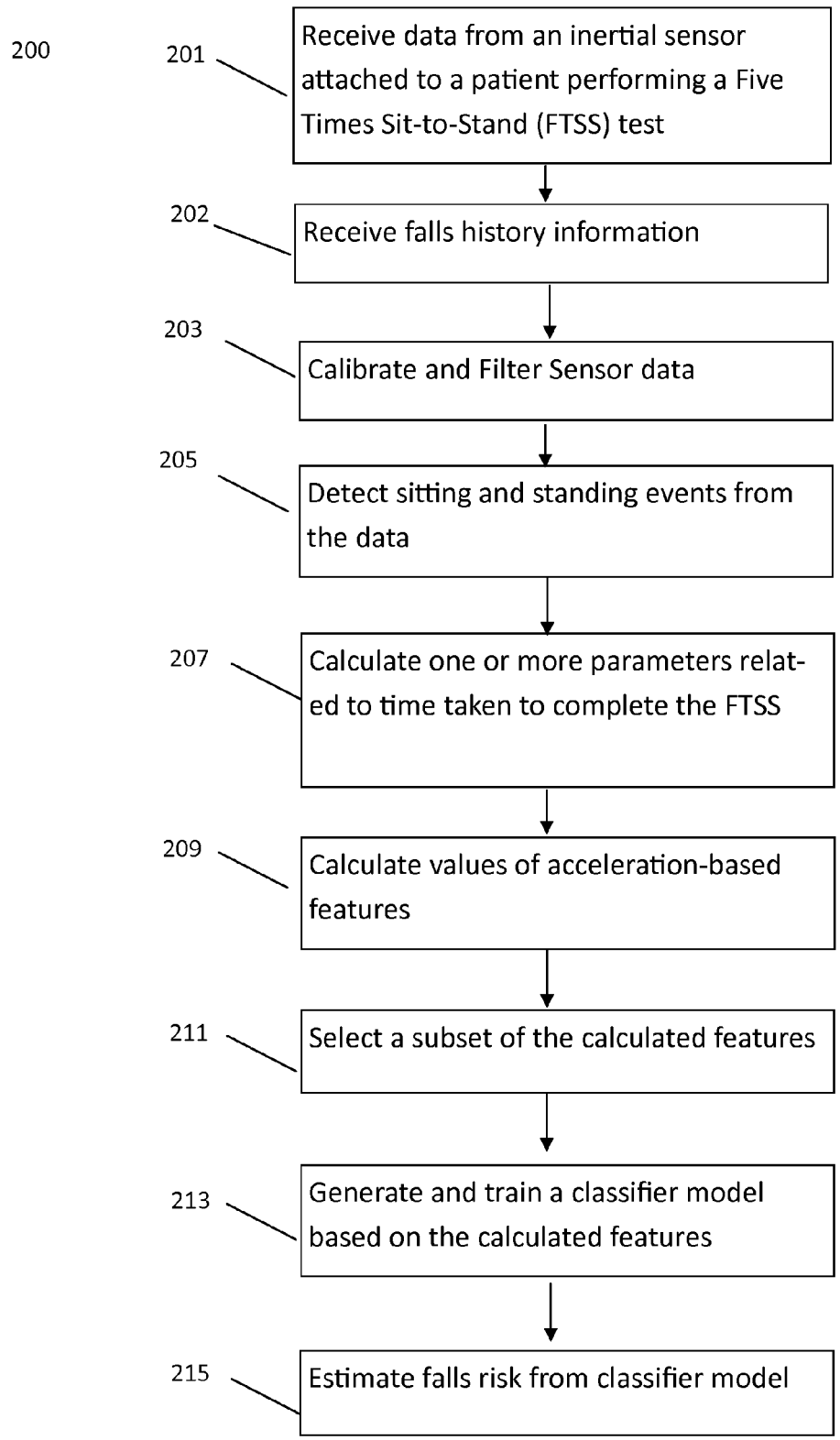
FIG. 2 illustrates example operations for estimating falls risk from inertial sensor data collected from a FTSS test.

FIG. 2 illustrates a method 200 for generating and training a classifier model for estimating falls risk based on FTSS-derived data.

At operation 201, data from one or more inertial sensors attached to a person performing a FTSS test may be received. For example, acceleration data may be received from accelerometers 103 and 105.

In an embodiment, data from the one or more inertial sensors may be collected through a single session, or may be collected through multiple sessions over a period of several minutes, hours, or days. For example, the inertial sensor data may be collected from a person who is asked to perform multiple FTSS tests throughout a single day.

At operation 202, self-reported falls history information of the person may be received. The falls history may indicate whether the person has experienced a fall, which may include coming to rest on a floor or other lower level, regardless of whether an injury was sustained. The falls history may exclude events that were a result of a major intrinsic event or overwhelming hazard. Based on a person's self-reported falls history, the person may be classified as a faller if he or she had experienced multiple falls or one fall requiring medical attention in the 12 months preceding the report. In an embodiment, a person may be classified as a faller based on falls before the previous 12 months if the falls were accompanied by more serious symptoms, such as a bone fracture or a blackout.

In an embodiment, values of clinical parameters, such as a person's age, BMI, and grip strength may be collected. In an embodiment, the person's gender may be recorded. An example of clinical parameter values among fallers and non-fallers is illustrated in Table 1. In the example, univariate analysis of variance (ANOVA) was used to compare the ages of fallers and non-fallers. The analysis showed no significant difference in age between fallers and non-fallers. One or more of the clinical parameters may be used as a feature in the classifier model.

TABLE 1

|   | Non-fallers (M/F) | Fallers (M/F) | Univariate analysis of variance |
|---|---|---|---|
| N | 9/11 | 7/12 | $p > 0.05$ |
| Age (yrs) | 70.43 ± 6.88/66.32 ± 4.42 | 74.41 ± 5.22/76.44 ± 8.28 | $p < 0.05$ |
| BMI (m/kg$^2$) | 28.62 ± 2.65/27.01 ± 2.76 | 25.35 ± 2.24/26.27 ± 4.54 | $p > 0.05$ |
| Grip (N) | 73.46 ± 30.88/57.83 ± 10.35 | 83.05 ± 12.19/35.03 ± 12.22 | $p > 0.05$ |

At operation 203, the received data may be calibrated and filtered to derive acceleration vectors with respect to unit axes of the one or more inertial sensors. For example, raw inertial sensor data from accelerometers 103 and 105 may be bandpass filtered with a frequency range of 0.1-5 Hz with a zero-phase 8$^{th}$ order Butterworth filter with a 50.2 Hz corner frequency. In an embodiment, the one or more inertial sensors may include a gyroscope.

Figure 3:
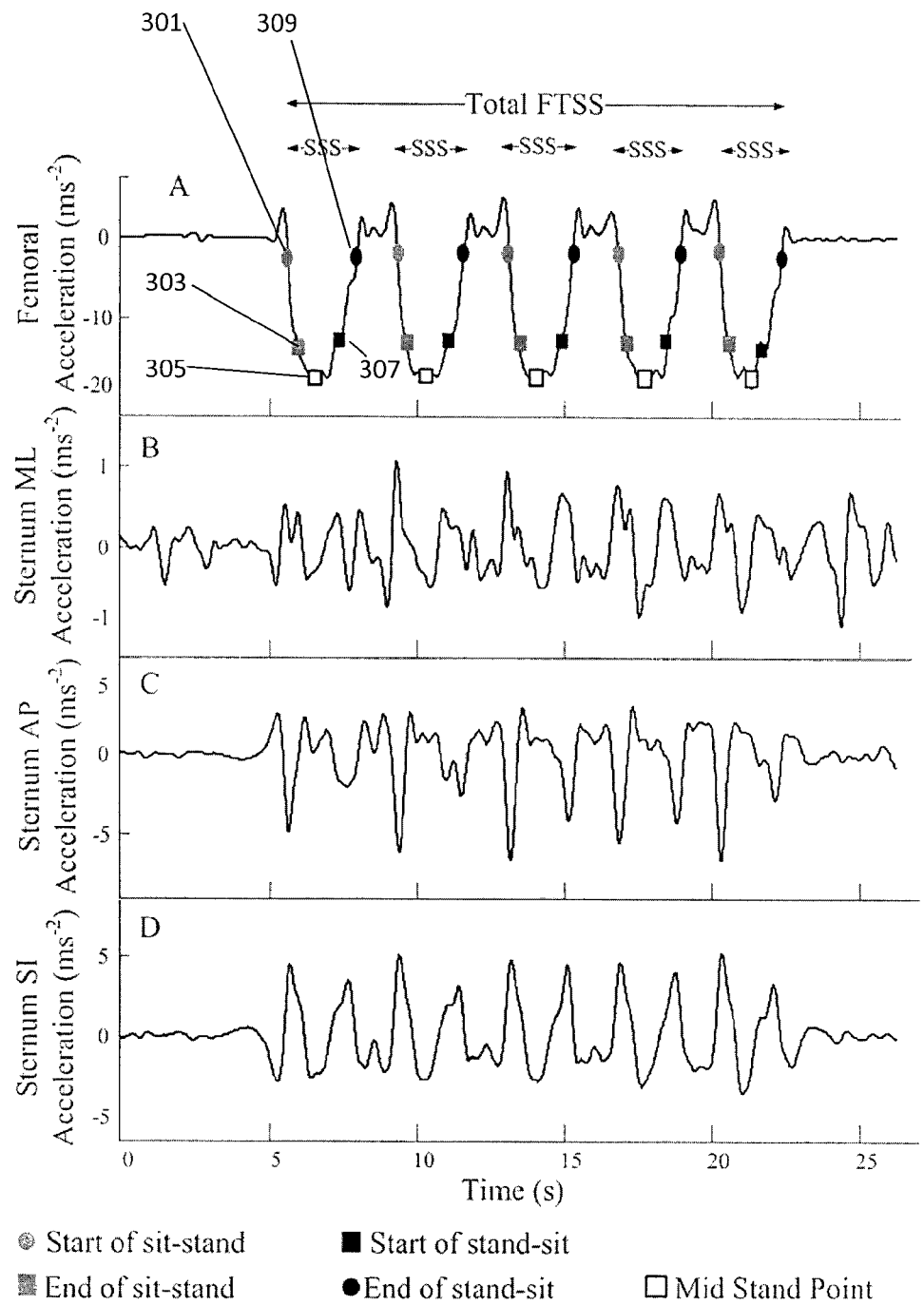
FIG. 3 illustrates example acceleration data collected from a FTSS test.

At operation 205, temporal events may be detected based on the inertial sensor data. For example, the acceleration data received from accelerometer 105, which is attached to a person's thigh, may be used to identify times at which the person performing the FTSS test was standing or was sitting, or to identify transitions between standing and sitting (or between sitting and standing). In an embodiment, such events may be determined based on identifying cycles in the acceleration data. As illustrated in FIG. 3, each cycle may include a point of minimum acceleration, or mid-stand point 305. A value of the mid-stand point 305 may be used to base a transition threshold between sitting and standing (or vice versa). For example, a threshold for indicating such transitions may be based on a percentage of the value of the mid-stand point 305. In a more specific example, transitions between sitting and standing may be based on thresholds of 20% and 80% of the mid-stand point value, or 0.2 $A_{MS}$ and 0.8 $A_{MS}$, respectively. In the example, a decrease in acceleration from zero (and an increase in absolute value) corresponds to a transition between sitting and standing. As illustrated in FIG. 3, decrease of the acceleration below 0.2 $A_{MS}$ indicates a start 301 of the transition between sitting and standing, while decrease of the acceleration past 0.8 $A_{MS}$ indicates an end 303 of the transition between sitting and standing. Past the mid-stand point, increase of the acceleration toward zero corresponds to a transition between standing and sitting. Increase of the acceleration past 0.8 $A_{MS}$ indicates a start 307 of a transition between standing and sitting, and increase of the acceleration above 0.2 $A_{MS}$ indicates an end 309 of the stand-sit transition. Data indicative of the person's femoral acceleration may thus identify cycles of sit-stand-sit (SSS) phases. Identification of the SSS phases, sit-stand transitions, and/or stand-sit transitions may allow other inertial sensor data to be corresponded to events in the FTSS test.

At operation 207, a value of one or more features or parameters related to timing of the FTSS may be calculated. The one or more parameters may include a total time taken to complete the FTSS, a time taken to complete individual sit-stand-sit (SSS) phases, or any other time-related feature. In an embodiment, the one or more features may include a time taken for a sit-stand transition (e.g., from start to finish) or for a stand-sit transition. In an embodiment, the one or more time-related features may be calculated based on sitting and standing events detected from the inertial sensor data. For example, the total time may be calculated as a difference between a time corresponding to the start of the first sit-stand transition and a time corresponding to the end of the fifth stand-sit transition, as detected from the femoral acceleration data.

At operation 209, a value of one or more features or parameters related to acceleration may be calculated. In an embodiment, the value may be calculated from the acceleration data measured by a sensor attached to a person's torso. For example, the acceleration data used in the calculation may be from sensor 103, which is attached above the person's sternum. In an embodiment, the one or more features may include an acceleration amplitude along a body axis (e.g., ML, AP, or SI axis), a jerk of the person's movement along a body axis, or a spectral edge frequency of the acceleration data along a body axis. The jerk of the person's movement may be calculated as a derivative of acceleration data along a sensor axis, and may measure steadiness of the person's movement along that axis. The spectral edge frequency, or SEF, of a signal may be calculated as the frequency below which 95% of the power of the signal is contained. In an embodiment, the one or more parameters may include statistical measures of the acceleration data, such as a mean, root mean squared (RMS), or CV of the acceleration amplitude or of the jerk along a body axis. The RMS of acceleration amplitude may measure sway in a person's movement.

At operation 211, a subset of the calculated features may be selected as input features of a classifier model. For example, sequential forward feature selection or stepwise feature selection may be used to select a subset of features that combine to best predict falls history. The technique may sequentially select features until there is no reduction in the unexplained variance (e.g., in Wilk's λ) of the classifier model. A F-test may be used as part of the technique. For example, the F-test may generate a value of a significance level of a feature to a classifier model. If the value is less than 0.05, the feature should not be entered into the model. Further, a feature should be removed from the classifier model if the value of the significance level is greater than 0.1. The removal and entry can be repeated until no feature meets the criteria for entry or removal.

In an embodiment, to provide performance measures reflecting robustness of a generated classifier model, leave-one-out cross-validation may be conducted to ensure that the selected subset of calculated features could be generalized to unseen data, so that the classifier model could be applicable to the population in general. For example, data from one FTSS participant may be used as validation data, and data from all other FTSS participants may be used as training data. The cross-validation may be repeated for each participant.

In an embodiment, to ensure that reliable and repeatable features are included in the model, test-retest reliability of each feature may be investigated. For example, if sensor data had been collected over multiple sessions, intra-class correlations, or ICC(2,k), may be calculated for the data collected over the multiple sessions. Features with ICC>0.4 may be considered acceptable for inclusion in the classifier model.

Table 2 illustrates example ICC values for various acceleration-based parameters.

TABLE 2

| Feature | ICC (95% CI) |
|---|---|
| Mean jerk ML stand-sit | 0.93 (0.88:0.96) |
| Mean jerk AP stand-sit | 0.92 (0.87:0.96) |
| CV RMS AP SSS | 0.90 (0.83:0.94) |
| CV RMS AP sit-stand | 0.89 (0.81:0.94) |
| Mean jerk SI stand-sit | 0.88 (0.80:0.94) |
| Mean jerk SI sit-stand | 0.87 (0.77:0.93) |
| Mean jerk AP SSS | 0.86 (0.77:0.93) |
| CV SEF ML sit-stand | 0.86 (0.69:0.95) |
| Mean jerk AP stand | 0.85 (0.74:0.92) |
| CV SEF AP sit-stand | 0.84 (0.64:0.94) |
| CV SEF SI sit-stand | 0.81 (0.57:0.93) |
| Mean jerk SI SSS | 0.79 (0.65:0.89) |
| Mean SEF ML sit-stand | 0.79 (0.64:0.88) |
| Mean SEF SI sit-stand | 0.77 (0.61:0.87) |
| Mean SEF AP sit-stand | 0.76 (0.59:0.87) |
| CV SEF SI SSS | 0.76 (0.59:0.87) |
| RMS SI total | 0.73 (0.55,0.85) |
| CV SEF ML stand-sit | 0.73 (0.33:0.92) |
| CV SEF ML SSS | 0.73 (0.54:0.85) |
| CV RMS SI SSS | 0.72 (0.52:0.85) |
| CV RMS ML stand-sit | 0.72 (0.52:0.85) |
| RMS AP total | 0.72 (0.52:0.84) |
| CV RMS SI sit-stand | 0.71 (0.52:0.84) |
| Mean jerk ML stand | 0.71 (0.51:0.84) |
| Mean SEF ML stand-sit | 0.71 (0.51:0.84) |
| Jerk AP total | 0.70 (0.49:0.84) |
| Mean SEF AP SSS | 0.70 (0.49:0.83) |
| CV SEF AP SSS | 0.68 (0.47:0.83) |
| Mean SEF SI SSS | 0.68 (0.46:0.82) |
| Mean RMS AP stand-sit | 0.67 (0.44:0.82) |
| Jerk SI total | 0.66 (0.43:0.82) |
| Mean jerk ML SSS | 0.66 (0.43:0.82) |
| Mean SEF AP stand-sit | 0.66 (0.43:0.81) |
| CV RMS ML SSS | 0.66 (0.43:0.81) |
| Mean SEF SI stand-sit | 0.66 (0.43:0.81) |
| CV RMS SI stand-sit | 0.66 (0.42:0.81) |
| CV RMS AP stand-sit | 0.65 (0.40:0.81) |
| CV SEF AP stand-sit | 0.65 (0.11:0.89) |
| Mean RMS SI sit-stand | 0.64 (0.40:0.81) |
| Mean RMS AP sit-stand | 0.64 (0.38:0.80) |
| Mean SEF ML SSS | 0.64 (0.38:0.80) |
| Mean RMS SI stand-sit | 0.63 (0.37:0.80) |
| Mean RMS SI SSS | 0.62 (0.36:0.79) |
| Mean RMS AP SSS | 0.60 (0.32:0.78) |
| Mean SSS time | 0.59 (0.31:0.78) |
| Total time | 0.58 (0.30:0.77) |
| CV RMS ML sit-stand | 0.58 (0.29:0.77) |
| CV SEF SI stand-sit | 0.56 (−0.10:0.87) |

TABLE 2-continued

| Feature | ICC (95% CI) |
|---|---|
| Mean RMS ML sit-stand | 0.56 (0.25:0.76) |
| CV jerk SI SSS | 0.56 (0.25:0.76) |
| SEF AP total | 0.55 (0.24:0.75) |
| Mean RMS ML stand-sit | 0.51 (0.17:0.73) |
| CV jerk SI stand | 0.51 (0.17:0.73) |
| Mean RMS ML SSS | 0.49 (0.14:0.72) |
| Mean sit-stand time | 0.47 (0.10:0.71) |
| SEF ML total | 0.44 (0.06:0.70) |
| SEF SI total | 0.35 (−0.10:0.65) |
| RMS ML total | 0.35 (−0.10:0.64) |
| Mean stand-sit time | 0.33 (−0.14:0.63) |
| CV sit-stand time | 0.30 (−0.18:0.62) |
| Jerk ML total | 0.23 (−0.30:0.58) |
| CV SSS time | 0.19 (−0.37:0.56) |
| CV stand-sit time | 0.18 (−0.39:0.55) |
| CV jerk ML stand | 0.15 (−0.44:0.53) |
| CV jerk ML stand-sit | 0.10 (−0.52:0.51) |
| CV jerk ML SSS | 0.03 (−0.65:0.47) |
| CV jerk AP stand-sit | −0.02 (−0.72:0.44) |
| CV jerk SI stand-sit | −0.03 (−0.74:0.44) |
| CV jerk AP SSS | −0.25 (−1.10:0.32) |
| CV jerk AP stand | −1.59 (−3.38:−0.42) |

Table 3 illustrates an example subset of features selected through sequential forward feature selection as input features to a classifier model.

TABLE 3

| Feature | Description |
|---|---|
| Mean jerk SI sit-stand (m/s$^3$) | Average jerk of the SI acceleration during each sit-stand transition. |
| Mean jerk ML SSS (m/s$^3$) | Average jerk of the ML acceleration during each SSS component. |
| CV SEF SI sit-stand (%) | Variance in spectral edge frequency of the SI acceleration for each sit-stand transition. |
| CV SEF ML SSS (%) | Variance in spectral edge frequency of the ML acceleration for each SSS component. |

In the example, features related to a person's sit-stand transition may be an indicator of falls risk. The sit-stand transition may relate to smoothness of a person's movement.

The classifier model may be trained to classify falls risk by associating values of the selected features derived from a sample of people performing FTSS tests with their self-reported falls history information. For example, a linear discriminant analysis may be used to calculate linear discriminant parameter values that best describes a relationship of feature values of various people and their self-reported falls history.

At operation 215, the trained classifier model may be used to estimate falls risk of people outside the sample.

In an embodiment, performance of a classifier model may be gauged through sensitivity, specificity, and accuracy of the model. Sensitivity may be calculated as a ratio of the number of fallers correctly classified as such compared to the total number of fallers. Specificity may be calculated as a ratio of the number of non-fallers correctly classified as such compared to the total number of non-fallers. Accuracy may be calculated as a ratio of the total number of test participants correctly classified compared to the total number of participants.

Figure 4:
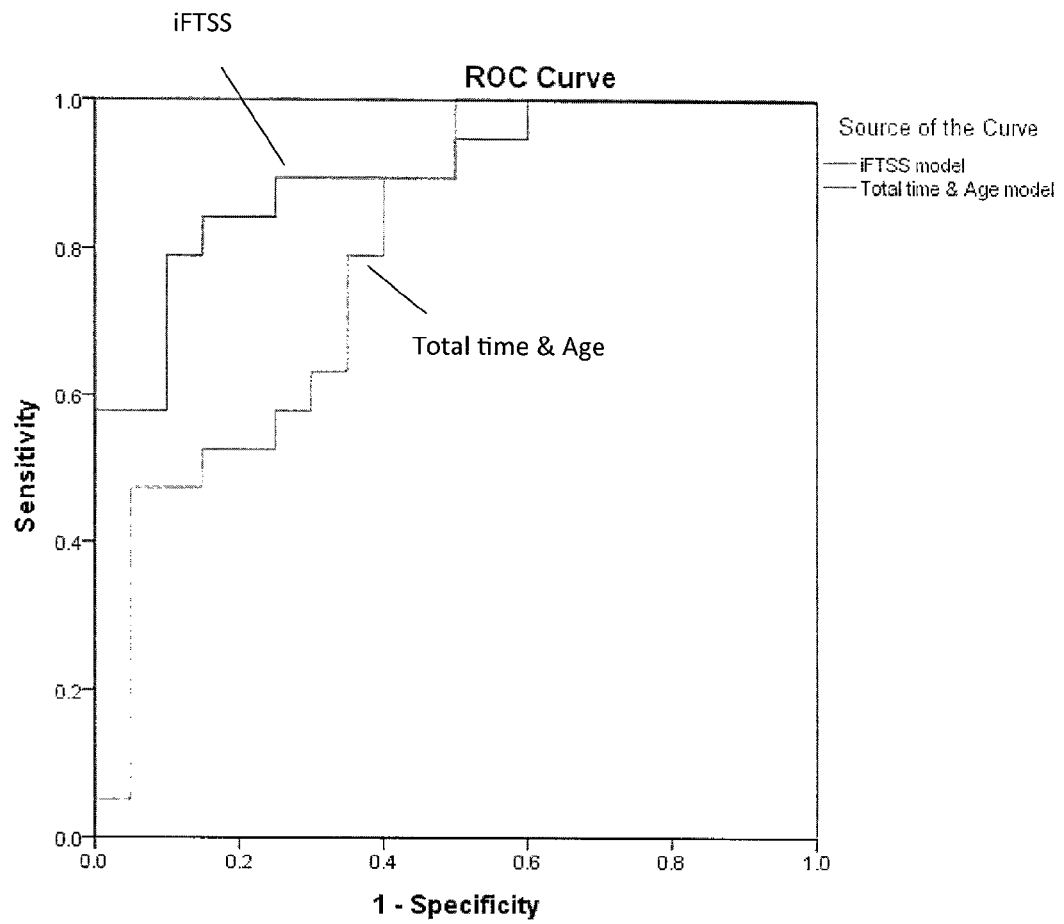
FIG. 4 illustrates example performance metric values of various falls risk estimation models.

In an embodiment, performance of a classifier model that is based on inertial sensor data may be compared to performance of a classifier model that is based solely on age and total FTSS time. A ROC analysis may be used for the comparison. The ROC curve analysis may allow evaluation of sensitivity and specificity for positive and negative results at various cutoff point levels of a dependent variable. As illustrated in FIG. 4, a ROC curve may be generated as a graphical representation of a relationship between sensitivity and false-positive rate (e.g., 1 minus specificity) across values of an independent or predictor variable. The area under the curve (AUC) of the ROC curve may be determined and tested against a null hypothesis of no discrimination (AUC=0.50). A ROC AUC significantly greater than 0.5 may indicate greater ability to classify a subject's falls history than would be predicted by chance.

Table 4 illustrates example values of the performance metrics described above for the classifier model based on the features illustrated in Table 3. For comparison, the table also illustrates example values of the performance metrics for a classifier model based on just ages and total FTSS time of people in the test sample.

TABLE 4

|  | Total time & Age | iFTSS |
|---|---|---|
| Accuracy | 64.1% | 82.1% |
| Sensitivity | 57.9% | 66.7% |
| Specificity | 70% | 95.2% |
| ROC AUC | 0.793 | 0.89 |

Figure 5:
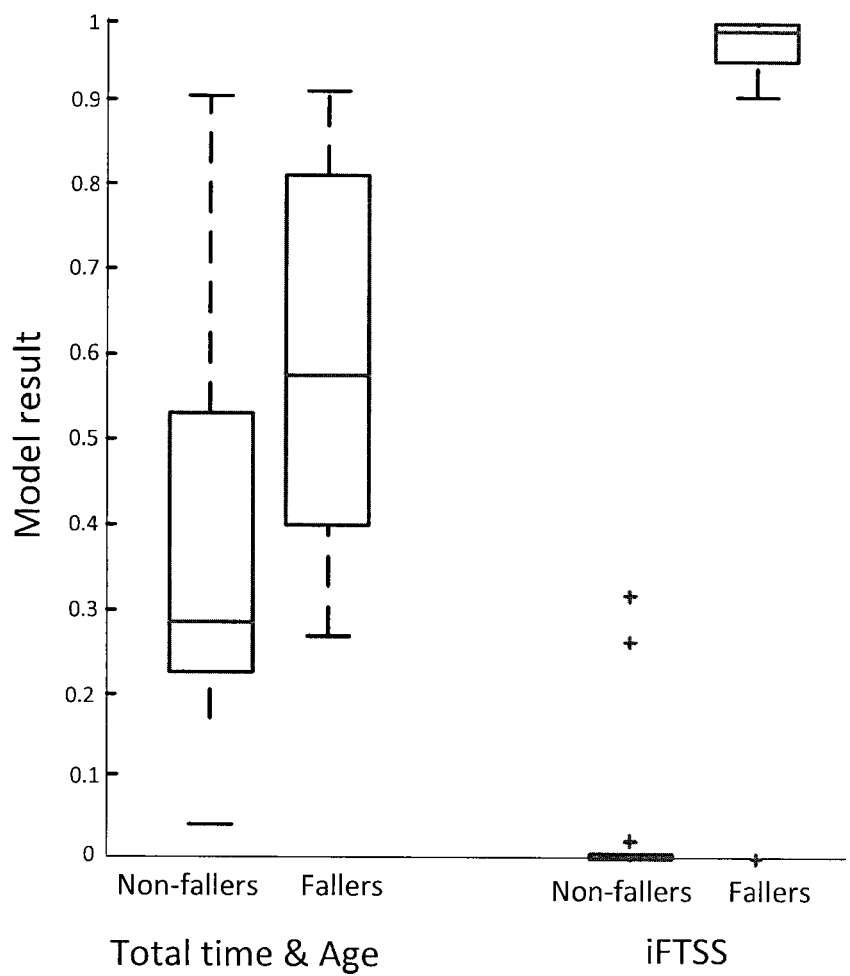
FIG. 5 illustrates example results generated by various falls risk estimation models.

In an embodiment, a classifier model may calculate a probability that a person will experience a fall, and may output a classification based on the calculated probability. FIG. 5 illustrates example probabilities outputted by classifier models, which use the probabilities to make a classification. In the illustration, the iFTSS-based classifier model generates a probability of close to 0 for most non-fallers and a probability of close to 1 for most fallers. In contrast, the classifier model based on total FTSS time and age generates probabilities that are more spread out.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

I claim:

1. A computer-implemented method for estimating falls risk, comprising:

measuring first acceleration data from a first inertial sensor and second acceleration data from a second inertial sensor, the first and second inertial sensors comprise tri-axial accelerometers and are attached to at least one person transitioning at least one times from a standing state to a sitting state or from a sitting state to a standing state, wherein the first inertial sensor is attached to the person's lower body and the second inertial sensor is attached to the person's upper body;

receiving, at one or more processors, the first acceleration data from the first inertial sensor attached to the at least one person;

receiving, at the one or more processors, the second acceleration data from the second inertial sensor attached to the at least one person;

receiving, at the one or more processors, falls history information of the at least one person;

determining, from the first acceleration data and using the one or more processors, a first value of one or more features indicating a total time for the at least one person to complete the transitioning between the sitting state and the standing state;

determining, from the second acceleration data and using the one or more processors, a second value of the one or more features indicating steadiness of movement of the at least one person, wherein a jerk of the at least one person's movement is calculated as a derivative of second acceleration data along a sensor axis to measure the steadiness of movement of the least one person along the sensor axis;

determining, from the second acceleration data and using the one or more processors, a third value of the one or more features indicating a mean, coefficient of variation, or root mean square of the second acceleration data and a fourth value of the one or more features indicating a spectral edge frequency of the second acceleration data;

generating, at the one or more processors, a classifier model based on the determined first value, the determined second value, the determined third value, the determined fourth value, and the falls history information of the at least one person;

after the generation of the classifier model, the one or more processors receiving acceleration data from inertial sensors attached to another person;

inputting a subset of the one or more features as input features of the classifier model;

calculating, via the one or more processors using both the generated classifier model and the received acceleration data from the another person, a quantitative value for a probability of a risk of falling of the another person; and outputting a classification of likely to fall or not being likely to fall for the another person based on the calculated probability using the one or more processors.

2. The computer-implemented method of claim 1, wherein the classifier model is a linear discriminant classifier model.

3. The computer-implemented method of claim 1, wherein the one or more processors further utilize the at least one person's age to generate the classifier model.

4. The computer-implemented method of claim 1, wherein the total time is calculated as a difference between a time corresponding to a start of a first transition and a time corresponding to an end of a fifth transition.

5. The computer-implemented method of claim 1, wherein the method further comprises calculating additional values based on the first and/or second acceleration data, the additional values indicating an acceleration amplitude along a person's body axis and a mean jerk of the person's movement along the person's body axis, and wherein the method further comprises using the additional values relating to the acceleration amplitude and the mean jerk to generate the classifier model.

6. The method of claim 1, wherein the first and second inertial sensors are attached to thigh and torso of the at least one person.

7. The method of claim 1, wherein the at least one times from a standing state to a sitting state or from a sitting state to a standing state comprises at least five times from a standing state to a sitting state or from a sitting state to a standing state.

8. A non-transitory computer-readable medium having instructions that, when executed by one or more processors, cause the one or more processors to:

receive first acceleration data from a first inertial sensor attached to at least one person transitioning at least one times from a standing state to a sitting state or from a sitting state to a standing state;

receive second acceleration data from a second inertial sensor attached to the at least one person taken during the transitioning at least one times, wherein the first and second inertial sensors comprise tri-axial accelerometers;

receive falls history information of the at least one person;

determine, from the first acceleration data, a first value of one or more features indicating a total time for the at least one person to complete the transitioning between the sitting state and the standing state;

determine, from the second acceleration data, a second value of one or more features indicating steadiness of movement of the at least one person;

determining, from the second acceleration data, a third value of one or more features indicating a mean, coefficient of variation, or root mean square of the second acceleration data and a fourth value of one or more features indicating a spectral edge frequency of the second acceleration data, wherein a jerk of the at least one person's movement is calculated as a derivative of second acceleration data along a sensor axis to measure the steadiness of movement of the least one person along the sensor axis;

generate a classifier model based on the determined first value, the determined second value, the determined third value, the determined fourth value, and the falls history information of the at least one person, wherein the first inertial sensor is attached to the person's lower body and the second sensor is attached to the person's upper body, and, after the generating of the classifier model, receiving acceleration data from inertial sensors attached to another person;

inputting a subset of the one or more features as input features of the classifier model;

calculating, using both the generated classifier model and the received acceleration data from the another person, a quantitative value for a probability of a risk of falling of the another person; and outputting a classification of likely to fall or not being likely to fall for the another person based on the calculated probability.

9. The non-transitory computer-readable medium of claim 8, wherein the instructions cause the one or more processors to generate a linear discriminant classifier model.

10. The non-transitory computer-readable medium of claim 8, wherein the one or more processors further utilize the at least one person's age to generate the classifier model.

11. The non-transitory computer-readable medium of claim 8, wherein the total time is calculated as a difference between a time corresponding to a start of a first transition and a time corresponding to an end of a fifth transition.

12. The non-transitory computer-readable medium of claim 8, wherein the method further comprises calculating additional values based on the first and/or second acceleration data, the additional values indicating an acceleration amplitude along a person's body axis and a mean jerk of the person's movement along the person's body axis, and wherein the method further comprises using the additional values relating to the acceleration amplitude and the mean jerk to generate the classifier model.

13. The method of claim 8, wherein the at least one times from a standing state to a sitting state or from a sitting state to a standing state comprises at least five times from a standing state to a sitting state or from a sitting state to a standing state.

* * * * *